United States Patent [19]

Matsumoto et al.

[11] Patent Number: 4,738,968
[45] Date of Patent: Apr. 19, 1988

[54] 1,8-NAPHTHYRIDINE DERIVATIVES USEFUL AS ANTI-BACTERIAL AGENTS

[75] Inventors: Jun-ichi Matsumoto; Junji Nakano, both of Ikoma; Katsumi Chiba, Osaka; Shinichi Nakamura, Takatsuki, all of Japan

[73] Assignee: Dainippon Pharmaceutical Co., Ltd., Osaka, Japan

[21] Appl. No.: 829,097

[22] Filed: Feb. 12, 1986

[30] Foreign Application Priority Data

Feb. 15, 1985 [JP] Japan .................................. 60-28998
Apr. 19, 1985 [JP] Japan .................................. 60-84985

[51] Int. Cl.$^4$ .................. A61K 31/435; C07D 471/04
[52] U.S. Cl. ..................................... 514/292; 546/123
[58] Field of Search .......................... 546/123; 514/292

[56] References Cited

U.S. PATENT DOCUMENTS 3,963,736  6/1976  Nakagome et al. ................ 546/123
4,382,937  5/1983  Matsumoto et al. ............... 546/123
4,665,079  5/1987  Culbertson et al. ............... 546/123

Primary Examiner—Henry R. Jiles
Assistant Examiner—J. Richter
Attorney, Agent, or Firm—Wenderoth, Lind & Ponack

[57] ABSTRACT

The present invention relates to a 1,8-naphthyridine derivative of the formula

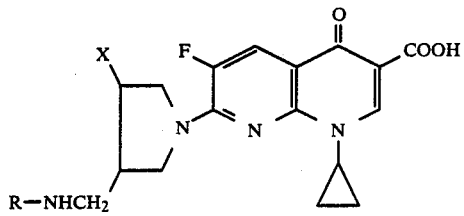

wherein X is a fluorine or chlorine atom, and R is a hydrogen atom, or a methyl or ethyl group;

and esters thereof and salts thereof are processes for preparation thereof. These compounds show excellent anti-bacterial activity and are useful antibacterial agents.

8 Claims, No Drawings

1,8-NAPHTHYRIDINE DERIVATIVES USEFUL AS ANTI-BACTERIAL AGENTS

This invention relates to novel 1,8-naphthyridine compounds having very high antibacterial activities and processes for preparing these novel compounds.

The compounds of this invention are 1,8-naphthyridine derivatives represented by the formula

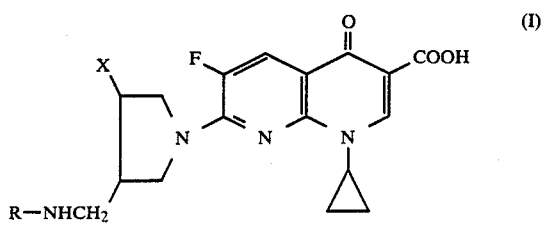

(I)

wherein X is a fluorine or chlorine atom, and R is a hydrogen atom, or a methyl or ethyl group; and esters and pharmaceutically acceptable salts thereof.

The salts of the compounds of the formula (I) or their esters may be any salt formed from the compounds of formula (I) or their esters with pharmaceutically acceptable acids or bases. The salts of the compounds of the invention are the salts derived from organic acids such as acetic acid, lactic acid, succinic acid, methanesulfonic acid, maleic acid, malonic acid, or gluconic acid; those from amino acids such as aspartic acid or glutamic acid; those from inorganic acids such as hydrochloric acid or phosphoric acid; metal (e.g. sodium, potassium, zinc, silver, etc.) salts; or organic base salts.

The esters of the compounds of formula (I) include not only the substituted or unsubstituted aliphatic esters, especially a lower alkyl esters having 1 to 5 carbon atoms such as a methyl or ethyl ester, but also esters that can be easily converted to the compounds (I) by hydrolysis or by enzymatic hydrolysis in vivo, such as an acetoxymethyl ester, a pivaloyloxymethyl ester, an ethoxycarbonyloxyethyl ester, a choline ester, aminoethyl esters (e.g. a dimethylaminoethyl ester, a 1-piperidinylethyl ester, etc.), a 5-indanyl ester, a phthalidyl ester, or hydroxyalkyl esters (e.g. a 2-hydroxyethyl ester, a 2,3-dihydroxypropyl ester, etc.).

The compounds of formula (I) and the esters and salts thereof will therefore all be generically referred to herein as the compounds of this invention.

The compounds of the invention may also exist as hydrates. Hence, these hydrates are also included in the compounds of the present invention.

The compounds of the invention have asymmetric carbon atoms on the pyrrolidine ring and therefore exist in optically active forms. Hence, they include D isomers, L isomers as well as mixtures thereof.

The compounds of the invention also have two asymmetric carbon atoms on the pyrrolidine ring, and therefore such compounds of the invention can exist as stereoisomers having different configurations (cis or trans form). These stereoisomers and their mixtures are also included in the compounds of this invention.

In the present specification, the compounds of the invention shown by their structures, in principle, represent all of the cis-isomers, trans-isomers, D-isomers, L-isomers and racemic mixtures inclusively. Particularly, the cis-isomers or trans-isomers will be specifically so designated.

The prior art on pharmaceutically effective compounds in this field will be discussed below.

U.S. Pat. No. 4,341,784 issued on July 27, 1982 discloses the following compounds with antibacterial activity.

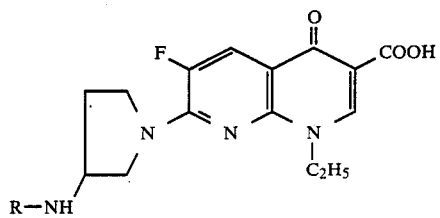

wherein R is hydrogen, methyl, ethyl or propyl.

But the compounds of this invention are surprisingly superior to the above known compounds in their antibacterial activity.

European Laid-Open Patent Specification No. 49355 published on Apr. 14, 1982 discloses the following general formula

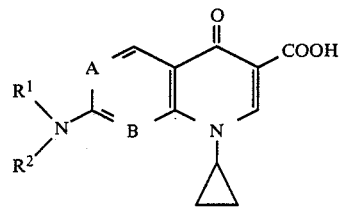

In regard to the group

shown in this formula, there is however no disclosure at all as to whether this is an aminomethyl and halogen-substituted pyrrolidinyl group.

European Laid-Open Patent Specifications No. 106489 published on Apr. 25, 1984 and No. 153163 published on Aug. 28, 1985 disclose a wide variety of compounds of the following general formula

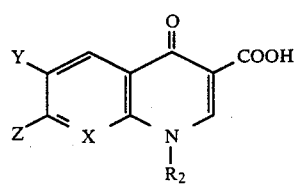

the definitions of $R_2$, X, Y and Z are omitted.

Among the compounds disclosed in the above specifications, the compound of the following formula (European Laid-Open Patent Specification No. 153163, Example 55) the following formula

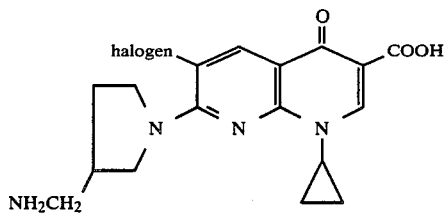

structurally most resembles the compounds of this invention. But there is no disclosure at all of any specific data on the antibacterial activity of this compound.

European Laid-Open Patent Specification No. 132845 published on Feb. 13, 1985 discloses the compounds of the formula

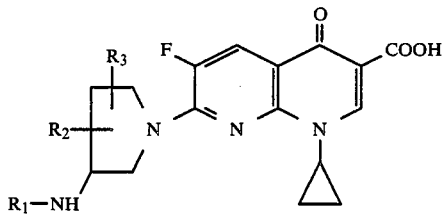

wherein $R_1$, $R_2$ and $R_3$ are hydrogen or lower alkyl group.

It is an object of the invention to provide novel 1,8-naphthyridine compounds (I) having high antibacterial activities against both Gram-positive bacteria and Gram-negative bacteria, as well as esters and pharmaceutically acceptable salts thereof, and processes for preparing these novel compounds.

Another object of the invention is to provide a pharmaceutical composition comprising an antibacterially effective amount of a compound selected from compounds having structural formula (I), and esters and pharmaceutically acceptable salts thereof.

The invention further provides a method for treating bacterial infectious diseases which comprises administering an antibacterially effective amount of the compound of this invention or the aforesaid pharmaceutical composition to warm-blooded aminals.

These and other objects of the invention will become apparent from the following description.

The compounds of this invention represented by formula (I) include the following compounds.

7-(3-Aminomethyl-4-fluoro-1-pyrrolidinyl)-1-cyclopropyl-6-fluoro-1,4-dihydro-4-oxo-1,8-naphthyridine-3-carboxylic acid (compound No. 1),

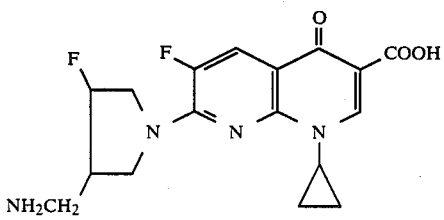

7-(3-Aminomethyl-4-chloro-1-pyrrolidinyl)-1-cyclopropyl-6-fluoro-1,4-dihydro-4-oxo-1,8-naphthyridine-3-carboxylic acid (compound No. 2),

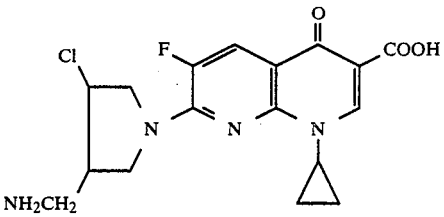

1-Cyclopropyl-6-fluoro-7-(4-fluoro-3-methylaminomethyl-1-pyrrolidinyl)-1,4-dihydro-4-oxo-1,8-naphthyridine-3-carboxylic acid (compound No. 3),

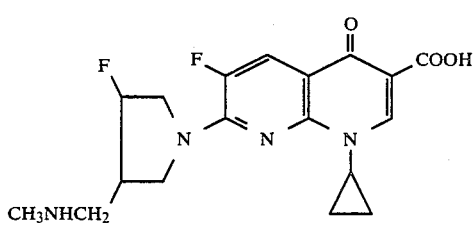

1-Cyclopropyl-7-(3-ethylaminomethyl-4-fluoro-1-pyrrolidinyl)-6-fluoro-1,4-dihydro-4-oxo-1,8-naphthyridine-3-carboxylic acid (compound No. 4),

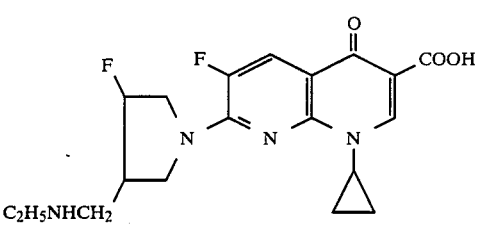

The compounds of this invention show excellent antibacterial activities and a broad antibacterial spectrum in in vitro tests. Furthermore, these compounds show an excellent infection-defending effect in vivo on systemic infections caused by Gram-positive and Gram-negative bacteria. These compounds have fairly good solubily in water.

The compounds of this invention are especially useful as parenteral antibacterial agents for systemic infections caused not only by Gram-negative bacteria but by Gram-positive bacteria.

The process for preparing the compounds of this invention will be described.

Process A: Displacement by pyrrolidine derivatives

The compounds of this invention can be prepared by reacting a carboxylic acid of the formula

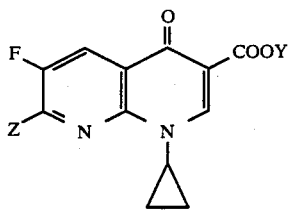

(II)

wherein Z is a reactive group replaceable by a nitrogen atom at position 1 of a pyrrolidine ring, and Y is a hydrogen atom or an aliphatic group,
or its ester, preferably a lower alkyl ester having 1 to 5 carbon atoms, with a pyrrolidine derivative of the formula

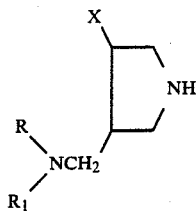

(III)

wherein X and R are the same as defined for formula (I), and $R_1$ is a hydrogen atom or a protective group for the amino group, and when a reaction product in which $R_1$ is a protective group for the amino group is obtained, removing the protective group.

The reactive functional groups shown by Z in formula (II) are halogen, arylsulfonyl, lower alkylsulfonyl having 1 to 5 carbon atoms, lower alkoxy having 1 to 5 carbon atoms, lower alkylthio having 1 to 5 carbon atoms, arylsulfinyl, lower alkylsulfinyl having 1 to 5 carbon atoms, arylsulfonyloxy, lower alkylsulfonyloxy having 1 to 5 carbon atoms, or the like, of which especially preferred are toluenesulfinyl, tuluenesulfonyl and halogen.

The reaction of the compound (II) with the compound (III) is carried out in an inert solvent such as ethanol, acetonitrile, dioxane, dimethylformamide, toluene or xylene, at 10°–180° C., preferably at 20°–150° C., for 5–120 minutes, usually for 20–60 minutes, with stirring.

The compound (III) is used in the amount equivalent to, or slightly in excess of, the amount of the compound (II). Depending upon the type of the functional group Z in the compound (II), the reaction results in producing an acid such as hydrochloric acid as a by-product. In such a case the reaction is generally carried out in the presence of an acid acceptor, but the compound (III) may be used in excess to make itself serve as an acid acceptor.

The protective groups shown by $R_1$ in the formula (III) are those commonly used in the chemistry of peptides, amino-sugars, nucleic acids, or β-lactam antibiotics. Any of these groups may be used so long as it can be removed without damaging the structure of the compounds of this invention formed by the reaction A. They can be split off by treatment with an acid or base or by reductive cleavage.

Examples of the protective group capable of being eliminated by treatment with acids or bases include acyl groups such as formyl, acetyl and trifluoroacetyl; substituted or unsubstituted alkoxycarbonyl groups such as ethoxycarbonyl, β, β, β-trichloroethoxycarbonyl, β-iodoethoxycarbonyl, benzyloxycarbonyl, p-methoxybenzyloxycarbonyl, t-butoxycarbonyl and β-(p-tolyenesulfonyl)ethoxycarbonyl; vinyloxycarbonyl group; trityl group; trialkylsilyl groups such as trimethylsilyl and t-butyldimethylsilyl; o-nitrophenylsulfenyl group; dihenylphosphinyl group; and tetrahydropyranyl group.

The treatment with an acid or base is carried out by contacting the displacement reaction product having a protective group with an acid or base at a temperature of 0° C. to 150° C.

Examples of the acid are inorganic acids such as hydrochloric acid, hydrobromic acid, sulfuric acid and phosphoric acid; organic acids such as acetic acid, trifluoroacetic acid, formic acid and p-toluenesulfonic acid; and Lewis acids such as boron trifluoride and aluminium chloride. Examples of the bases are alkali metal hydroxides such as sodium hydroxide and barium hydroxide; alkali metal carbonates such as sodium carbonate and potassium carbonate; alkali metal alkoxides such as sodium methoxide and sodium ethoxide; sodium acetate; and zinc.

The treatment with an acid or base is carried out in the presence or absence of water depending upon the type of the amino protective group. For example, when the amino protective group is an easily hydrolyzable group such as acetyl, trifluoroacetyl or ethoxycarbonyl it can be easily removed by treatment with the acid or base in the presence of water (i.e., hydrolysis). The reaction is usually carried out in water, but a mixture of water with a solvent such as ethanol, dioxane, ethylene glycol dimethyl ether, benzene or acetic acid may also be used.

The other protective groups stated above may also be removed by hydrolysis. Trityl, t-butoxycarbonyl, o-nitrophenylsulfonyl, and the like may also be removed by treatment with an acid such as hydrochloric acid, formic acid, acetic acid or trifluoroacetic acid in a substantially anhydrous condition. Trimethylsilyl and the like may also be removed by contacting with an alcohol such as methanol or ethanol. β, β, β-Trichloroethoxycarbonyl, β-iodoethoxycarbonyl, and the like may also be removed by treatment with zinc in a solvent such as acetic acid.

Examples of the protective group capable of being eliminated by reduction include arylsulfonyl groups such as p-toluenesulfonyl; phenyl- or benzyloxy-substituted methyl groups such as benzyl, trityl and benzyloxymethyl; arylmethoxycarbonyl groups such as benzyloxycarbonyl and p-methoxybenzyloxycarbonyl.

The reducing reaction is carried out by treating the protected compound with a hydrogen stream in an inert solvent at 10° to 60° C. in the presence of a catalyst such as platinum, palladium, Raney nickel or the like, or with metallic sodium in liquid ammonia at −50° to −20° C. Solvents for the catalytic reduction include ethylene-glycol dimethyl ether, dioxane, dimethylformamide, ethanol, ethyl acetate, and acetic acid.

The starting compound (II) is prepared in accodance with the method described in Reference Example 1 given hereinafter. The starting compound (III) is prepared in accordance with the methods described in Reference Examples 2 to 6.

The esters of the compounds (I) prepared by the Process A as mentioned above can be converted to the compounds (I) (carboxylic acids) by hydrolysis in accordance with reaction B described below. The compounds (I), if necessary, may be esterified by a conventional method to give the esters of the compounds (I).

Process B: Acid or base treatment and reductive cleavage

The compounds of formula (I) can also be prepared by treating a compound of the formula

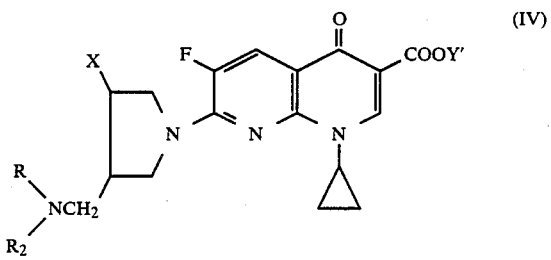

wherein Y' is a hydrogen atom or an aliphatic group, $R_2$ is a hydrogen atom or a protective group for the amino group, provided that Y' and $R_2$ are not hydrogen atoms at the same time, and X and R are the same as defined above,
with an acid or base, and/or reducing the compound (IV).

The acid or base treatment and reductive treatment can be performed in the same way as described above with regard to Process A.

The starting compound (IV) may be produced by, for example, using a compound of formula (II) in which Y is an aliphatic group or a compound of formula (III) in which $R_1$ is an amino-protective group in accordance with the displacement reaction in Process A.

The pharmaceutically acceptable salts of the compound (I) or its ester are prepared by treating the compound (I) or its ester with an acid, or the compound (I) with a base or a metal salt. Examples of suitable acids are hydrochloric acid, phosphoric acid, acetic acid, lactic acid, succinic acid, methanesulfonic acid, maleic acid, malonic acid, gluconic acid, aspartic acid and glutamic acid. Examples of suitable bases or metal salts are metal hydroxides such as sodium or potassium hydroxide, metal carbonates such as sodium or potassium carbonate, zinc chloride, zinc sulfate, zinc nitrate and silver nitrate.

The compounds of the invention thus prepared are isolated and purified in a conventional manner. Depending upon the conditions of isolation and/or purification, the compounds are obtained in the form of a salt or in a free form. These compounds can however be transformed from one form to another to meet the purpose for which they are to be used. Thus, the compounds of this invention are prepared into a form that meets their intended use.

The stereoisomers (cis and trans forms) of the compounds of the invention can be isolated by a conventional method such as fractional crystallization or chromatography. Again, by using the compounds (III) of cis or trans forms as the starting material and submitting them to the reaction of process A of this invention, it is possible to obtain the compounds of this invention having the corresponding configurations.

The compounds of the invention can also exist in optically active forms which may be obtained separately by an optical resolution procedure known in the art.

The compounds (I), their esters and their salts thus obtained are all new. Especially, the compounds (I) have excellent antibacterial activity and therefore are valuable as antibacterial agents. The compounds (I) and their salts can be used not only as medicines for man and animals, but as fish medicines, agricultural chemicals and food preservatives. On the other hand, the esters of the compounds (I) are useful as starting material for preparation of the compounds (I). They are also useful as antibacterial agents because they themselves have high antibacterial activity and where the ester is easily transformed to the compound (I) in vivo, it shows the same antibacterial effect as the compound (I).

The dosage of the compounds of the invention in administration to man should be adjusted according to the age, body weight, symptoms, etc. of a patient, the administration route, etc. It is recommended that the compound be administered at a dosage of 5 mg to 5 g per day once or several times daily. The compound may be administered orally or parenterally.

The compounds of the invention may be administered in its as-obtained powder form, but it is usually administered in the form of a pharmaceutical preparation together with pharmaceutically acceptable adjuvants. Specific examples are tablets, solutions, capsules, granules, fine granules, powders, syrups, injections, ointments, etc. These pharmaceutical preparations are prepared in a customary manner. Adjuvants for oral administrations are those that are commonly used in the field of pharmaceutical preparation and do not react with the compounds of the invention, such as starch, mannitol, crystalline cellulose, CMC Na, etc. Adjuvants for injections are those commonly used in the field of injection such as water, isotonic sodium chloride solution, glucose solution, transfuction solution, etc. When the compound of this invention is to be used as an injection, it can be used for all of such injections as intravenous, intramsucular and subcutaneous injections.

Solutions and ointments such as described above can also be used for local treatments in oto-rhino-larynglogy or ophthalmology.

The following Examples 1 to 13 and Reference Examples 1 to 6 will serve to illustrate the processes for preparing the compounds of the present invention.

REFERENCE EXAMPLE 1

7-Chloro-1-cyclopropyl-6-fluoro-1,4-dihydro-4-oxo-1,8-naphthyridine-3-carboxylic acid and its ethyl ester

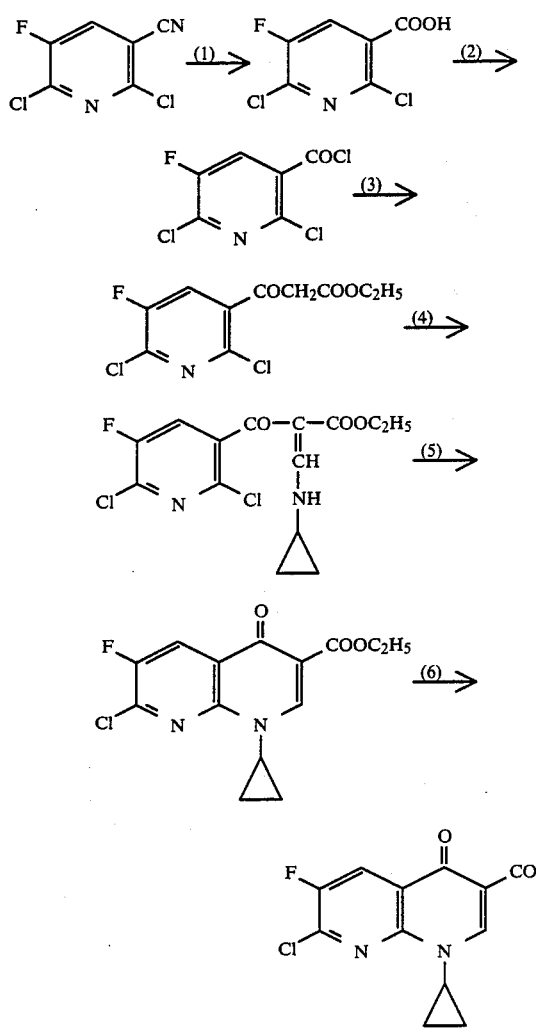

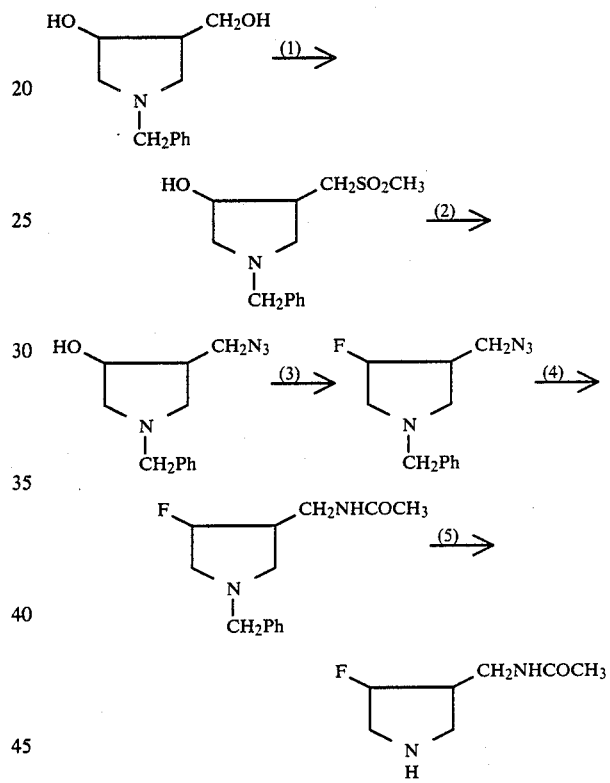

The numbers of the reaction steps described below correspond to the numbers in the above scheme.

(1) The known compound, 2,6-dichloro-5-fluoronicotinonitrile (60 g) was heated at 65°–75° C. for 1 hour in concentrated sulfuric acid. After addition of water, the mixture was further heated at 100°–110° C. for 2 hours to give 2,6-dichloro-5-fluoronicotinic acid (59.8 g), m.p. 155°–156° C.

(2) The above compound (45.2 g) was treated with thionyl chloride to give 2,6-dichloro-5-fluoronicotinoyl chloride (47.5 g) as an oil.

(3) The above compound (47.5 g) was allowed to react with diethyl ethoxymagnesium malonate in dry ether to yield diethyl 2,6-dichloro-5-fluoronicotinoylmalonate as an oil. To this compound were added water and a catalytic amount of p-toluenesulfonic acid and the mixture was heated at 140° C. for 2 hours to give ethyl 2,6-dichloro-5-fluoronicotinoylacetate (46 g), m.p. 69°–70° C.

(4) The above compound (12 g) was treated with ethyl orthoformate and acetic anhydride to yield ethyl 2-(2,6-dichloro-5-fluoronicotinoyl)-3-ethoxyacrylate. This compound was allowed to react in ethanol with cyclopropylamine and triethylamine at room temperature to give ethyl 3-cyclopropylamino-2-(2,6-dichloro-5-fluoronicotinoyl)acrylate (12.7 g), m.p. 129°–130° C.

(5) The above compound (12 g) was allowed to react in dry dioxane with potassium t-butoxide to yield ethyl 7-chloro-1-cyclopropyl-6-fluoro-1,4-dihydro-4-oxo-1,8-naphthyridine-3-carboxylate (10 g), m.p. 176°–178° C.

(6) The above compound (9 g) was hydrolyzed with 20% hydrochloric acid to give 7-chloro-1-cyclopropyl-6-fluoro-1,4-dihydro-4-oxo-1,8-naphthyridine-3-carboxylic acid (8 g), m.p. 222°–223.5° C.

Reference Example 2 cis- and trans-3-Acethylaminomethyl-4-fluoropyrrolidine

The numbers of the reaction steps described below correspond to the numbers in the above scheme.

(1) The known compound, 1-benzyl-3-hydroxy-4-hydroxymethylpyrrolidine [see J. Org. Chem., 30, 740 (1965)] (110 g) was allowed to react in chloroform with methanesulfonyl chloride (60.9 g) in the presence of triethylamine to yield 1-benzyl-3-hydroxy-4-methanesulfonyloxymethylpyrrolidine (81 g) as an oil.

IR spectrum (film) cm$^{-1}$: 3370, 1350, 1170.

Mass spectrum m/z: 285 (M+), 208, 190, 91.

(2) The above compound (50 g) was allowed to react in dimethylformamide with sodium azide (22.8 g) at 120°–130° C. to yield 3-azidomethyl-1-benzyl-4-hydroxypyrrolidine (30 g).

IR spectrum (film) cm$^{-1}$: 3350, 2100, 1450, 1265.

Mass spectrum m/z: 232 (M+), 175, 158, 91.

(3) The above compound (32 g) in chloroform was treated with hexafluoropropene-diethylamine reagent (64 g) to yield a crude product, which was chromatographed on silia gel to give the following products. trans-3-Azidomethyl-1-benzyl-4-fluoropyrrolidine (3.5 g) as an early fraction.

IR spectrum (film) cm$^{-1}$: 2100, 1450, 1270.
Mass spectrum m/z: 234 (M+), 177, 91.
NMR spectrum (CDCl$_3$) δ: 3.64 (2H, s, C$\underline{H_2}$Ph), 4.5 and 5.2 (1H, br, C$_4$-H), 7.30 (5H, s, C$_6$H$_5$).

cis-3-Azidomethyl-1-benzyl-4-fluoropyrrolidine (3.0 g) as a later fraction.

IR spectrum (film) cm$^{-1}$: 2100, 1450, 1270.
Mass spectrum m/z: 234 (M+), 177, 91.
NMR spectrum (CDCl$_3$) δ: 3.68 (2H, s, C$\underline{H_2}$Ph), 4.75 and 5.45 (1H, br, C$_4$-H), 7.30 (5H, s, C$_6$H$_5$).

A mixture of cis- and trans-3-azidomethyl-1-benzyl-4-fluoropyrrolidine (7.3 g) was obtained as a middle fraction.

(4) The above compound (trans) (3.1 g) was reduced with sodium bis-(2-methoxyethoxy)aluminium hydride and then acetylated to give trans-3-acetylaminomethyl-1-benzyl-4-fluoropyrrolidine (2.2 g) as an oil.

IR spectrum (film) cm$^{-1}$: 3270, 1650, 1550.
Mass spectrum m/z: 250 (M+), 158, 91.
NMR spectrum (CDCl$_3$) δ: 1.96 (3H, s, COCH$_3$), 3.61 (2H, s, C$\underline{H_2}$Ph), 4.52 and 5.22 (1H, br, C$_4$-H), 7.30 (5H, s, C$_6$H$_5$).

In the same manner as described above, cis-3-acetylaminomethyl-1-benzyl-4-fluoropyrrolidine was obtained as an oil from the above compound (cis).

IR spectrum (film) cm$^{-1}$: 3270, 1650, 1550.
Mass spectrum m/z: 250 (M+), 158, 91.
NMR spectrum (CDCl$_3$) δ: 1.98 (3H, s, COCH$_3$), 3.66 (2H, s, C$\underline{H_2}$Ph), 4.75 and 5.48 (1H, br, C$_4$-H), 7.31 (5H, s, C$_6$H$_5$).

In the same manner as described above, a mixture of cis- and trans-3-acetylaminomethyl-1-benzyl-4-fluoropyrrolidine was obtained from a mixture of cis- and trans-3-azidomethyl-1-benzyl-4-fluoropyrrolidine.

(5) The above compound (trans) was dissolved in ethanol and hydrogenolyzed in the presence of 5% palladium-carbon catalyst. After removing the catalyst by filtration, an ethanol solution containing trans-3-acetylaminomethyl-4-fluoropyrrolidine was obtained. This solution was then used in the following displacement reaction.

In the same manner as described above, a solution containing cis-3-acetylaminomethyl-4-fluoropyrrolidine was obtained from the above compound (cis).

In the same manner as described above, a solution containing cis- and trans-3-acetylaminomethyl-4-fluoropyrrolidine was obtained from a mixture of cis- and trans-3-acetylaminomethyl-1-benzyl-4-fluoropyrrolidine.

EXAMPLE 1

7-(trans-3-Aminomethyl-4-fluoro-1-pyrrolidinyl-1-cyclopropyl-6-fluoro-1,4-dihydro-4-oxo-1,8-naphthyridine-3-carboxylic acid hydrochloride (compound No. 1 - trans. hydrochloride)

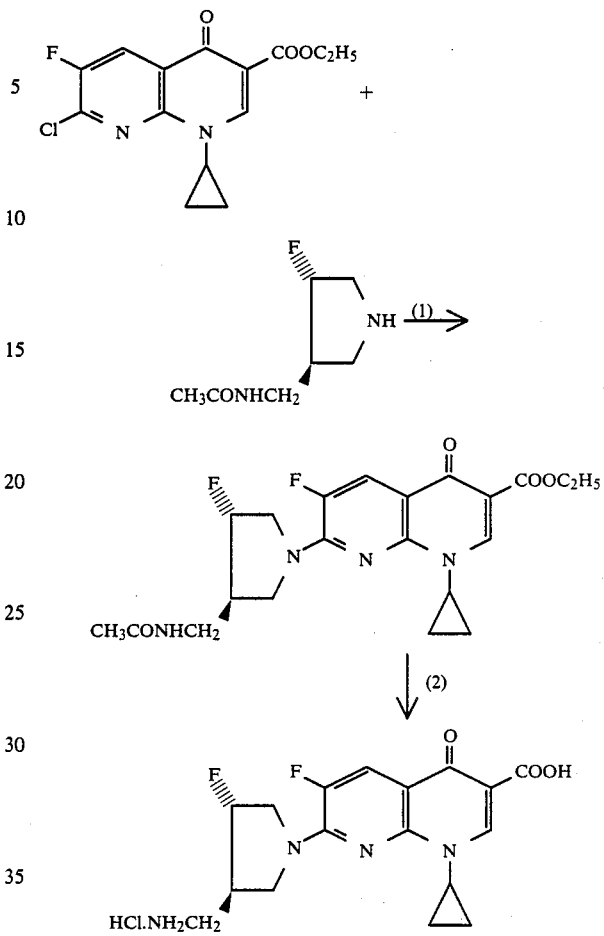

The numbers of the reaction steps described below correspond to the numbers in the above scheme.

(1) trans-3-Acetylaminomethyl-1-benzyl-4-fluoropyrrolidine (2.2 g) was dissolved in ethanol (50 ml), and 5% palladium-carbon (0.3 g) was added. The mixture was hydrogenolyzed at 60°-70° C. under hydrogen stream. After removing the catalyst by filtration, ethyl 7-chloro-1-cyclopropyl-6-fluoro-1,4-dihydro-4-oxo-1,8-naphthyridine-3-carboxylate (2.2 g) and triethylamine (3 ml) were added to the filtrate and the mixture was refluxed for 2 hours. After evaporation of the solvent, water was added to the residue and the mixture was extracted with chloroform. The extract was dried, the solvent was evaporated, and the resulting residue was chromatographed on silica gel to give ethyl 7-(trans-3-acetylaminomethyl-4-fluoro-1-pyrrolidinyl)-1-cyclopropyl-6-fluoro-1,4-dihydro-4-oxo-1,8-naphthyridine-3-carboxylate (1.3 g), m.p. 211°-213° C.

(2) A mixture of the above compound (1.3 g) and 15% hydrochloric acid (40 ml) was refluxed for 3 hours. Hydrochloric acid was evaporated under reduced pressure, the residue was dissolved in a small amount of water and the solution was cooled. The resulting crystals were collected by filtration to give 7-(trans-3-aminomethyl-4-fluoro-1-pyrrolidinyl)-1-cyclopropyl-6-fluoro-1,4-dihydro-4-oxo-1,8-nahthyridine-3-carboxylic acid hydrochloride (0.75 g), m.p. 269°–272° C. (decomp.).

EXAMPLE 2

7-(cis-3-Aminomethyl-4-fluoro-1-pyrrolidinyl-1-cyclopropyl-6-fluoro-1,4-dihydro-4-oxo-1,8-naphthyridine-3-carboxylic acid and its hydrochloride (compound No. 1 cis and its hydrochloride)

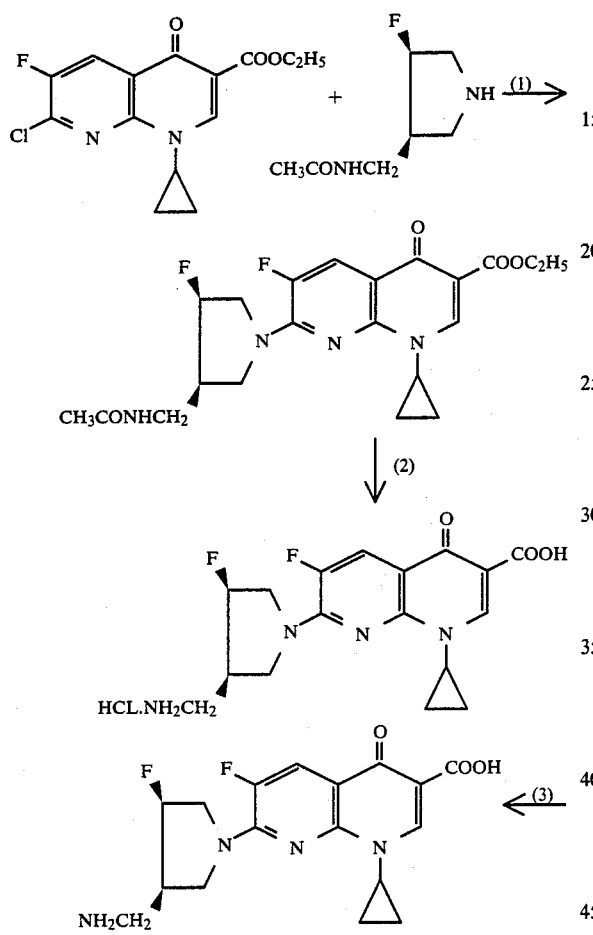

The numbers of the reaction steps described below correspond to the numbers in the above scheme.

(1) In the same manner as described in Example 1-(1) except that cis-3-acetylaminomethyl-1-benzyl-4-fluoropyrrolidine was used in place of trans-3-acetylaminomethyl-1-benzyl-4-fluoropyrrolidine, ethyl 7-(cis-3-acetylamino-methyl-4-fluoro-1-pyrrolidinyl)-1-cyclopropyl-6-fluoro-1,4-dihydro-4-oxo-1,8-naphthyridine-3-carboxylate was obtained. m.p. 179°–181° C.

(2) In the same manner as described in Example 1-(2), 7-(cis-3-aminomethyl-4-fluoro-1-pyrrolidinyl)-1-cyclopropyl-6-fluoro-1,4-dihydro-4-oxo-1,8-naphthyridine-3-carboxylic acid hydrochloride was prepared from the above compound. m.p. 284°–286° C. (decompn.).

(3) To the above hydrochloride was added concentrated aqueous ammonia and the mixture was made to faintly alkaline. After cooling, the crystals were collected by filtration to give 7-(cis-3-aminomethyl-4-fluoro-1-pyrrolidinyl)-1-cyclopropyl-6-fluoro-1,4-dihydro-4-oxo-1,8-naphthyridine-3-carboxylic acid, m.p. 217°–218° C.

Reference Example 3 cis- and trans-3-Acetylaminomethyl-4-chloropyrrolidine

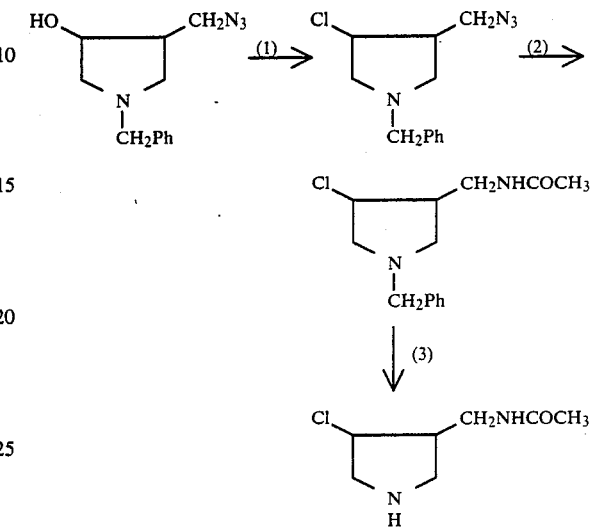

The numbers of the reaction steps described below correspond to the numbers in the above scheme.

(1) 3-Azidomethyl-1-benzyl-4-hydroxypyrrolidine was treated in chloroform with thionyl chloride and the crude product was fractionated by chromatography to give the following products.

cis-3-Azidomethyl-1-benzyl-4-chloropyrrolidine
IR spectrum (film) cm$^{-1}$: 2800, 2100, 740, 700.
Mass spectrum m/z: 250 (M$^+$), 158, 91.
NMR spectrum (CDCl$_3$) δ: 2.6 (1H, m, C$_3$-H), 2.5–3.0 (2H, m, C$_2$-H), 2.8–3.4 (2H, m, C$_5$-H), 3.3–3.7 (2H, m, CH$_2$N$_3$), 3.73 (2H, s, CH$_2$Ph), 4.5 (1H, m, C$_4$-H), 7.34 (5H, s, C$_6$H$_5$).

trans-3-Azidomethyl-1-benzyl-4-chloropyrrolidine
IR spectrum (film) cm$^{-1}$: 2800, 2100, 740, 700.
Mass spectrum m/z: 250 (M$^+$), 158, 91.
NMR spectrum (CDCl$_3$) δ: 2.58 (1H, m, C$_3$-H), 2.45–2.8 (2H, m, C$_2$-H), 2.8–3.2 (2H, m, C$_5$-H), 3.44 (2H, m, CH$_2$N$_3$), 3.66 (2H, br s, CH$_2$Ph), 4.05 (1H, m, C$_4$-H), 7.34 (5H, s, C$_6$H$_5$).

(2) The above compound (cis) was reduced with sodium bis-(2-methoxyethoxy)aluminium hydride and then treated with acetic anhydride and aqueous sodium hydroxide solution to yield cis-3-acetylaminomethyl-1-benzyl-4-chloropyrrolidine as an oil.
IR spectrum (film) cm$^{-1}$: 3300, 2800, 1650, 700.
Mass spectrum m/z: 266 (M$^+$), 231, 171, 158, 91.
NMR spectrum (CDCl$_3$) δ: 1.97 (3H, s, COCH$_3$), 2.5–2.9 (2H, m, C$_2$-H), 2.72 (1H, m, C$_3$-H), 2.8–3.3(2H, m, C$_5$-H), 3.3–3.7 (2H, m, CH$_2$NHCOCH$_3$), 3.71 (2H, s, CH$_2$Ph), 4.48 (1H, m, C$_4$-H), 7.33 (5H, s, C$_6$H$_5$).

In the same manner as described above, from the above compound (trans), trans-3-acetylaminomethyl-1-benzyl-4-chloropyrrolidine was obtained as an oil.

IR spectrum (film) cm$^{-1}$: 3300, 2800, 1650, 700.
Mass spectrum m/z: 266 (M+), 231, 158, 91.
NMR spectrum (CDCl$_3$) δ: 1.97 (3H, s, COCH$_3$), 2.3–2.8 (3H, m, C$_2$-H and C$_3$-H), 3.03–3.75 (4H, m, CH$_2$NHCOCH$_3$ and C$_5$-H), 3.6 (2H, s, CH$_2$Ph), 4.1 (1H, m, C$_4$-H), 7.3 (5H, s, C$_6$H$_5$).

(3) The above compound (cis) in ethanol was hydrogenolyzed in the presence of 5% palladium-carbon and acetic acid. After filtration of the catalyst, the filtrate was concentrated under reduced pressure to give cis-3-acetylaminomethyl-4-chloropyrrolidine as an oil.

In the same manner as described above, trans-3-acetylaminomethyl-4-chloropyrrolidine was obtained from the above compound (trans).

EXAMPLE 3

7-(cis-3-Aminomethyl-4-chloro-1-pyrrolidinyl)-1-cyclopropyl-6-fluoro-1,4-dihydro-4-oxo-1,8-naphthyridine-3-carboxylic acid and its hydrochloride (Compound No. 2 -cis and its hydrochloride)

1,8-naphthyridine-3-carboxylate (4.6 g), m.p. 213°–214° C.

(2) A mixture of the above compound (2.0 g) and 20% hydrochloric acid (20 ml) was refluxed for 2 hours. Hydrochloric acid was evaporated under reduced pressure and ethanol was added to the residue. The resulting crystals were collected by filtration to give 7-(cis-3-aminomethyl-4-chloro-1- pyrrolidinyl)-1-cyclopropyl-6-fluoro-1,4-di-hydro-4-oxo-1,8-naphthyridine-3-carboxylic acid hydrochloride (1.55 g), m.p. 243°–248° C. (decompn.).

(3) The above compound (1.0 g) was dissolved in water. To this solution was added saturated aqueous sodium bicarbonate solution to adjust the solution at pH 7.5–8.0 and cooled. The crystals were filtered off and recrystallized from chloroform-ethanol to give 7-(cis-3-aminomethyl-4-chloro-1-pyrrolidinyl)-1-cyclopropyl-6-fluoro-1,4-dihydro-4-oxo-1,8-naphthyridine-3-carboxylic acid (0.7 g), m.p. 174°–177° C.

The numbers of the reaction steps described below correspond to the numbers in the above scheme.

(1) cis-3-Acetylaminomethyl-1-benzyl-4-chloropyrrolidine (3.5 g) was dissolved in ethanol (40 ml). To the solution were added acetic acid (2 ml) and 5% palladiumcarbon (0.3 g) and the mixture was hydrogenolyzed. After absorption of the calculated amount of hydrogen, the catalyst was filtered off and the filtrate was concentrated under reduced pressure. The resulting oily cis-3-acetylaminomethyl-4-chloropyrrolidine was dissolved in acetonitrile (50 ml). Ethyl 7-chloro-1-cyclopropyl-6-fluoro-1,4-dihydro-4-oxo-1,8-naphthyridine-3-carboxylate (3.3 g) and triethylamine (8 ml) were added to the solution and the mixture was refluxed for 1 hour. After standing at room temperature overnight, the crystals were filtered and then dissolved in a mixture of water and chloroform. The mixture was shaken, and the chloroform layer was separated, dried, and evaporated. The residue was recrystallized from acetonitrile to give ethyl 7-(cis-3-acetylaminomethyl-4-chloro-1-pyrrolidinyl)-1-cyclopropyl-6-fluoro-1,4-dihydro-4-oxo-

EXAMPLE 4

7-(trans-3-Aminomethyl-4-chloro-1-pyrrolidinyl)-1-cyclopropyl-6-fluoro-1,4-dihydro-4-oxo-1,8-naphthyridine-3-carboxylic acid (Compound No. 2-trans)

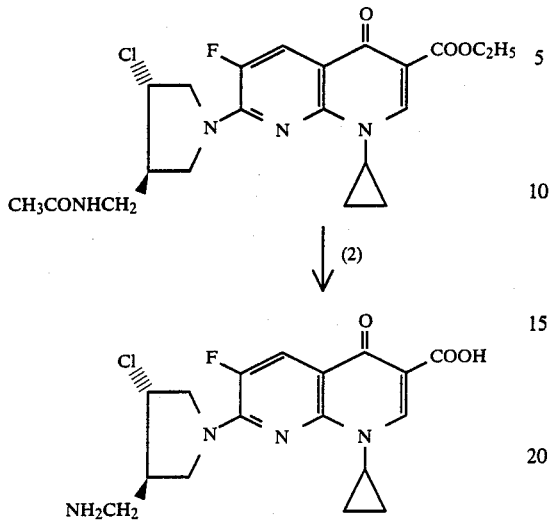

The numbers of the reaction steps described below correspond to the numbers in the above scheme.

(1) In the same manner as described in Example 3-(1), except that trans-3-acetylaminomethyl-1-benzyl-4-chloropyrrolidine was used in place of cis-3-acetylaminomethyl-1-benzyl-4-chloropyrrolidine, ethyl 7-(trans-3-acetylaminomethyl-4-chloro-1-pyrrolidinyl)-1-cyclopropyl-6-fluoro-1,4-dihydro-4-oxo-1,8-naphthyrine-3-carboxylate was obtained. m.p. 203°–206° C.

(2) In the same manner as described in Examples 3-(2) and 3-(3), 7-(trans-3-aminomethyl-4-chloro-1-pyrrolidinyl)-1-cyclopropyl-6-fluoro-1,4-dihydro-4-oxo-1,8-naphthyridine-3-carboxylic acid was obtained from the above compound. m.p.222°–224° C. (decompn.).

REFERENCE EXAMPLE 4 cis-4-Fluoro-3-(N-methyltrifluoroacetylaminomethyl)pyrrolidine

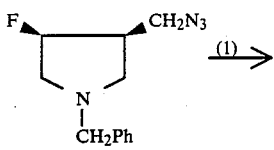

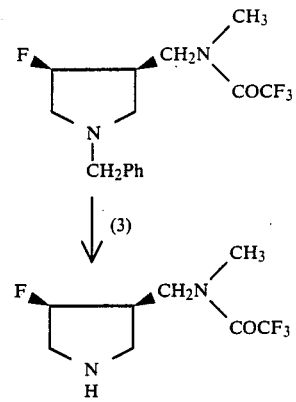

The numbers of the reaction steps described below correspond to the numbers in the above scheme.

(1) cis-3-Azidomethyl-1-benzyl-4-fluoropyrrolidine was reduced with sodium bis-(2-methoxyethoxy)aluminium hydride and formylated with formic acid-acetic anhydride to yield cis-1-benzyl-4-fluoro-3-formylaminomethylpyrrolidine.

(2) The above compound was reduced with sodium bis-(2-methoxyethoxy)aluminium hydride and then treated with trifluoroacetic anhydride to yield cis-1-benzyl-4-fluoro-3-(N-methyltrifluoroacetylaminomethyl)pyrrolidine as an oil.

IR spectrum (film) cm$^{-1}$: 1690, 1190.

Mass spectrum m/z: 318 (M$^+$), 241, 158, 91.

NMR spectrum (CDCl$_3$) δ: 3.68 (2H, s, C$\underline{H_2}$Ph), 5.00 (1H, br d, J=51 Hz, C$_4$-H), 7.30 (5H, s, C$_6$$\underline{H_5}$).

(3) The above compound was treated in the same manner as described in Example 3-(3) to give cis-4-fluoro-3-(N-methyltrifluoroacetylaminomethyl)pyrrolidine.

EXAMPLE 5

1-Cyclopropyl-6-fluoro-7-(cis-4-fluoro-3-methylaminomethyl-1-pyrrolidinyl)-1,4-dihydro-4-oxo-1,8-naphthyridine-3-carboxylic acid (Compound No. 3 - cis)

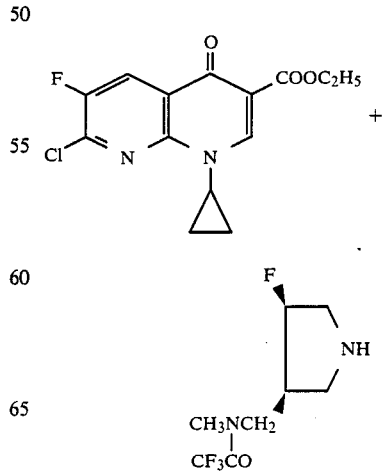

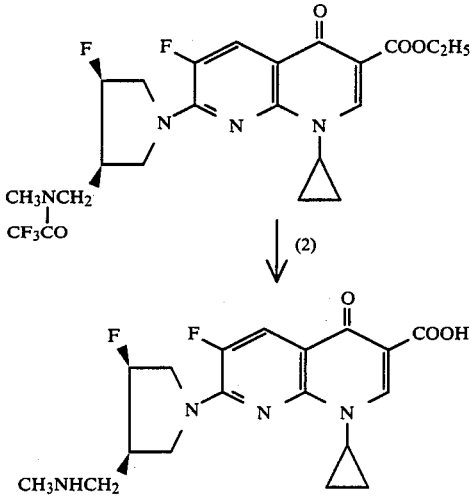

The numbers of the reaction steps described below correspond to the numbers in the above scheme.

(1) In the same manner as described in Example 3-(1) except that cis-1-benzyl-4-fluoro-3-(N-methyltrifluoroacetylaminomethyl)pyrrolidine was used in place of cis-3-acetylaminomethyl-1-benzyl-4-chloropyrrolidine, ethyl 1-cyclopropyl-6-fluoro-7-[cis-4-fluoro-3-(N-methyltrifluoroacetylaminomethyl)-1-pyrrolidinyl]-1,4-dihydro-4-oxo-1,8-naphthyridine-3-carboxylate was obtained. m.p. 177°–179° C.

(2) The above compound was heated in a 10% aqueous sodium hydroxide solution at 90°–100° C. for 1.5 hours. The reaction mixture was adjusted to pH 7.5–8.0 by addition of aqueous acetic acid. The resulting crystals were collected by filtration to give 1-cyclopropyl-6-fluoro-7-(cis-4-fluoro-3-methylaminomethyl-1-pyrrolidinyl)-1,4-dihydro-4-oxo-1,8-naphthyridine-3-carboxylic acid. m.p. 230°–240° C.

Reference Example 5 cis- and trans-4Fluoro-3-(N-ethyltrifluoroacetylaminomethyl)pyrrolidine

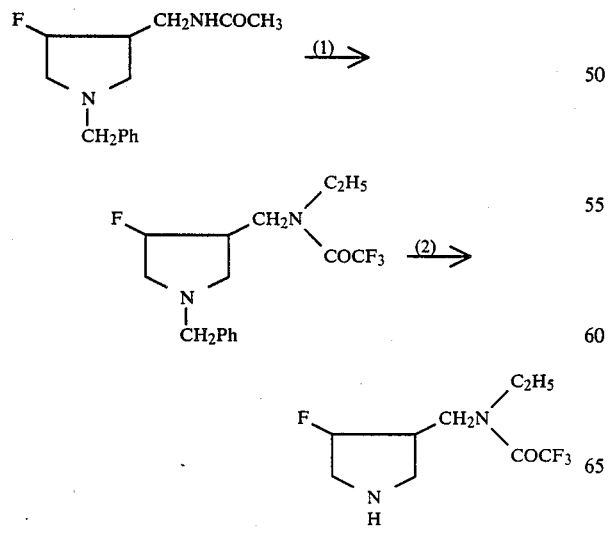

The numbers of the reaction steps described below correspond to the numbers in the above scheme.

(1) cis-3-Acetylaminomethyl-1-benzyl-4-fluoropyrrolidine was treated in the same manner as described in Reference Example 4-(2) to give cis-1-benzyl-4-fluoro-3-(N-ethyltrifluoroacetylaminomethyl)pyrrolidine as an oil.

IR spectrum (film) cm$^{-1}$: 1690, 1140.

Mass spectrum m/z: 332 (M+), 255, 158, 91.

NMR spectrum (CDCl$_3$) δ: 5.10 (1H, br d, J=60 Hz, C$_4$-H), 7.33 (5H, s, C$_6$H$_5$).

In the same manner as described above, trans-1-benzyl-4-fluoro-3-(N-ethyltrifluoroacetylaminomethyl)pyrrolidine was obtained as an oil from trans-3-acetylaminomethyl-1-benzyl-4-fluoropyrrolidine.

IR spectrum (film) cm$^{-1}$: 1690, 1190, 1145.

Mass spectrum m/z: 332 (M+), 255, 235, 91.

NMR spectrum (CDCl$_3$) δ: 1.26 (3H, t J=7 Hz), 4.90 (1H, br d, J=52 Hz, C$_4$-H), 7.34 (5H, s, C$_6$H$_5$).

(2) The above compound (cis) was treated in the same manner as described in Reference Example 3-(3) to give cis-4-fluoro-3-(N-ethyltrifluoroacetylaminomethyl)pyrrolidine.

In the same manner as described above, trans-4-fluoro-3-(N-ethyltrifluoroacetylaminomethyl)pyrrolidine was obtained from the above compound (trans).

EXAMPLE 6

1-Cyclopropyl-7-(cis-3-ethylaminomethyl-4-fluoro-1-pyrrolidinyl)-6-fluoro-1,4-dihydro-4-oxo-1,8-naphthyridine-3-carboxylic acid hydrochloride (compound naphthyridine-3-carboxylic acid hydrochloride (compound No. 4-cis.hydrochloride)

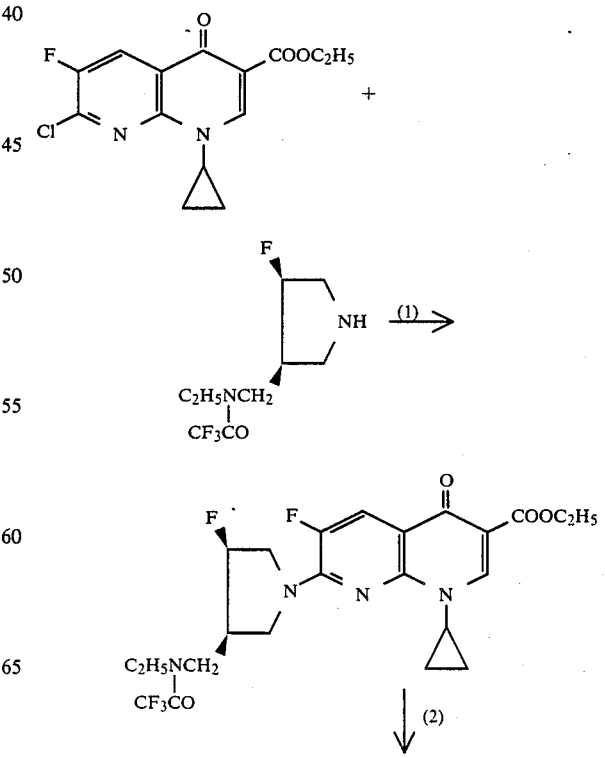

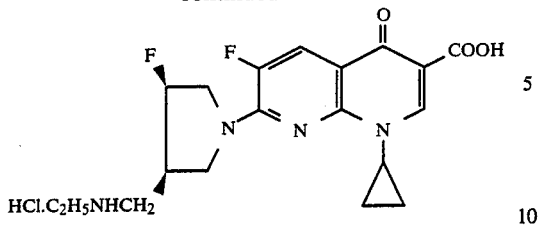

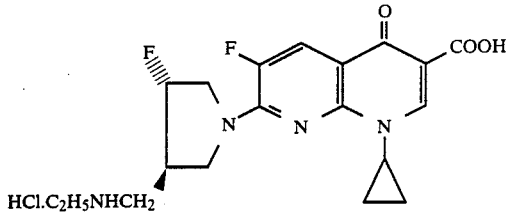

The numbers of the reaction steps described below correspond to the numbers in the above scheme.

(1) In the same manner as described in Example 3-(1) except using cis-1-benzyl-3-(N-ethyltrifluoroacetylaminomethyl)-4-fluoropyrrolidine in place of cis-3-acetylaminomethyl-1-benzyl-4-chloropyrrolidine, ethyl 1-cyclopropyl-7-[cis-3-(N-ethyltrifluoroacetylaminomethyl)-4-fluoro-1-pyrrolidinyl]-6-fluoro-1,4-dihydro-4-oxo-1,8-naphthyridine-3-carboxylate was obtained, m.p. 198°–200° C.

(2) The above compound was hydrolyzed in the same manner as described in Example 5-(2). The reaction mixture was then acidified with hydrochloric acid and concentrated. The resulting crystals were filtered to give 1-cyclopropyl-7-(cis-3-ethylaminomethyl-4-fluoro-1-pyrrolidinyl)-6-fluoro-1,4-dihydro-4-oxo-1,8-naphthyridine-3-carboxylic acid hydrochloride, m.p. 275°–280° C.

EXAMPLE 7

1-Cyclopropyl-7-(trans-3-ethylaminomethyl-4-fluoro-1-pyrrolidinyl)-6-fluoro-1,4-dihydro-4-oxo-1,8-naphthyridine-3-carboxylic acid hydrochloride (compound No. 4-trans.hydrochloride)

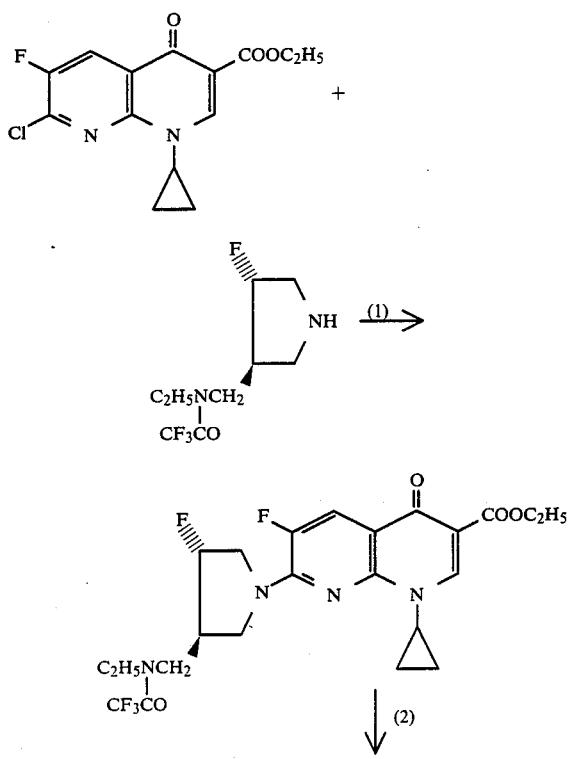

The numbers of the reaction steps described below correspond to the numbers in the above scheme.

(1) In the same manner as described in Example 3-(1) except using trans-1-benzyl-3-(N-ethyltrifluoroacetylaminomethyl)-4-fluoropyrrolidine in place of cis-3-acetylaminomethyl-1-benzyl-4-chloropyrrolidine, ethyl 1-cyclopropyl-7-[trans-3-(N-ethyltrifluoroacetylaminomethyl)-4-fluoro-1-pyrrolidinyl]-6-fluoro-1,4-dihydro-4-oxo-1,8-naphthyridine-3-carboxylate was obtained, m.p. 150°–153° C.

(2) The above compound was hydrolyzed in the same manner as described in Example 5-(2). The reaction mixture was acidified with hydrochloric acid and concentrated. The resulting crystals were collected by filtration to give 1-cyclopropyl-7-(trans-3-ethylaminomethyl-4-fluoro-1-pyrrolidinyl)-6-fluoro-1,4-dihydro-4-oxo-1,8-naphthyridine-3-carboxylic acid hydrochloride, m.p. 268°–270° C.

REFERENCE EXAMPLE 6 trans-3-(Acetyl-N-ethylaminomethyl)-4-fluoropyrrolidine

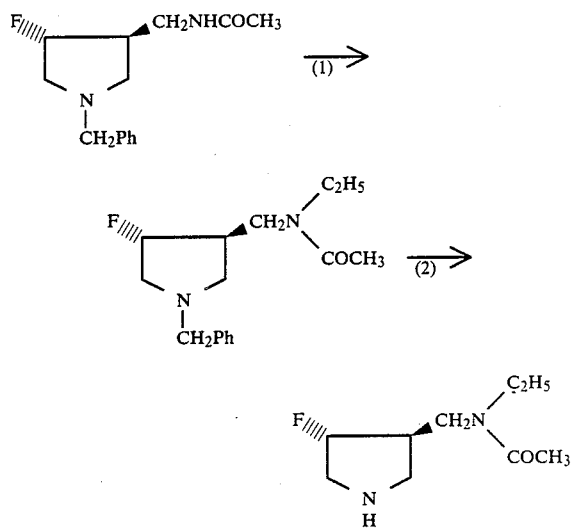

The numbers of the reaction steps described below correspond to the numbers in the above scheme. (1) trans-3-Acetylaminomethyl-1-benzyl-4-fluoropyrrolidine was reduced with sodium bis-(2-methoxyethoxy)aluminum hydride and acetylated with acetic anhydride to yield trans-3-(acetyl-N-ethylaminomethyl)-1-benzyl-4-fluoropyrrolidine as an oil.

IR spectrum (film) cm$^{-1}$: 1630, 1450, 1420.
Mass spectrum m/z: 278 (M$^+$), 258, 158, 91.

NMR spectrum (CDCl$_3$) δ: 1.18 (3H, t, J=7 Hz, CH$_2$ CH$_3$), 2.10 (3H, s, COCH3), 3.61 (2H CH$_2$Ph), 4.88 (1H, br d, J=56 Hz, C$_4$-H), 7.30 (5H, s, C$_6$H$_5$).

(2) The above compound was treated in the same manner as described in Example 3-(3) to give trans-3-(acetyl-N-ethylaminomethyl)-4-fluoropyrrolidine.

EXAMPLE 8

1-Cyclopropyl-7-(trans-3-ethylaminomethyl-4-fluoro-1-pyrrolidinyl)-6-fluoro-1,4-dihydro-4-oxo-1,8-naphthyridine-3-carboxylic acid hydrochloride (compound No. 4-trans.hydrochloride)

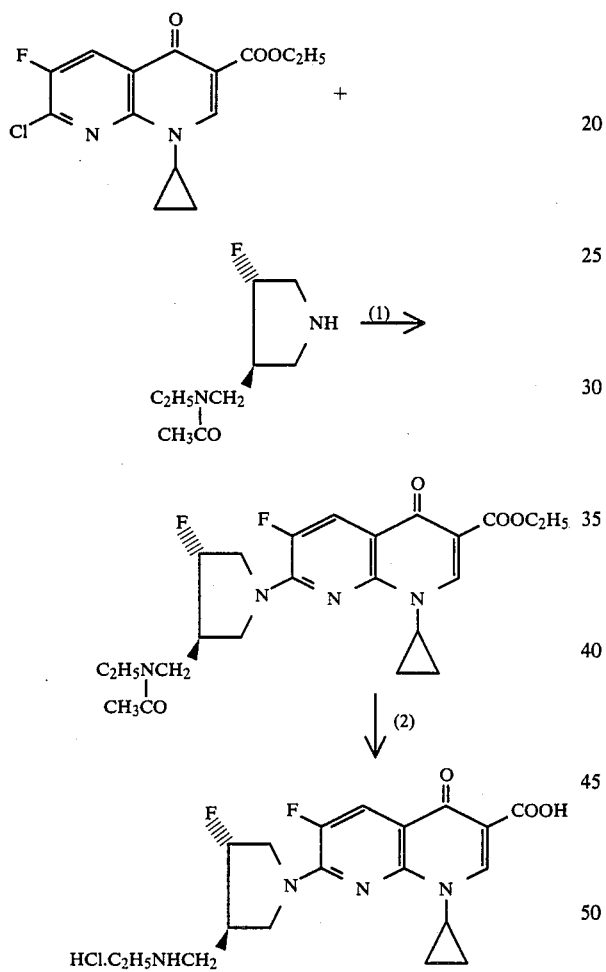

The numbers of the reaction steps described below correspond to the numbers in the above scheme.

(1) In the same manner as described in Example 3-(1) except using trans-3-(acetyl-N-ethylaminomethyl)-1-benzyl-4-fluoropyrrolidine in place of cis-3-acetylaminomethyl-1-benzyl-4-chloropyrrolidine, ethyl 1-cyclopropyl-7-[trans-3-(N-ethylacetylaminomethyl)-4-fluoro-1-pyrrolidinyl]-6-fluoro-1,4-dihydro-4-oxo-1,8-naphthyridine-3-carboxylate was obtained, m.p. 105°-107° C.

(2) In the same manner as described in Example 3-(2), 1-cyclopropyl-7-(trans-3-ethylaminomethyl-4-fluoro-1-pyrrolidinyl)-6-fluoro-1,4-dihydro-4-oxo-1,8-naphthyridine-3-carboxylic acid hydrochloride was obtained from the above compound, m.p. 268°-270° C.

EXAMPLE 9

7-(cis-3-Aminomethyl-4-chloro-1-pyrrolidinyl)-1-cyclopropyl-6-fluoro-1,4-dihydro-4-oxo-1,8-naphthyridine-3-carboxylic acid hydrochloride (compound No. 2-cis.hydrochloride)

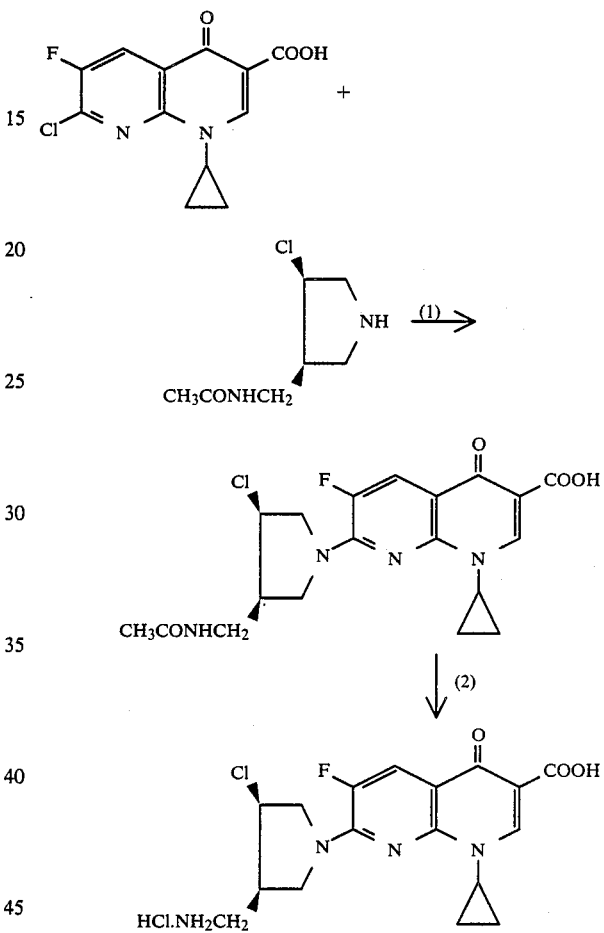

The numbers of the reaction steps described below correspond to the numbers in the above scheme.

(1) In the same manner as described in Example 3-(1), 7-(cis-3-acetylaminomethyl-4-chloro-1-pyrrolidinyl)-1-cyclopropyl-6-fluoro-1,4-dihydro-4-oxo-1,8-naphthyridine-3-carboxylic acid was obtained from cis-3-acetylaminomethyl-1-benzyl-4-chloropyrrolidine and 7-chloro-1-cyclopropyl-6-fluoro-1,4-dihydro-4-oxo-1,8-naphthyridine-3-carboxylic acid. m.p. 236°-242° C. (decompn.).

(2) In the same manner as described in Example 3-(2), 7-(cis-3-aminomethyl-4-chloro-1-pyrrolidinyl)-1-cyclopropyl-6-fluoro-1,4-dihydro-4-oxo-1,8-naphthyridine-3-carboxylic acid hydrochloride was obtained from the above compound. m.p. 243°-248° C. (decompn.).

EXAMPLE 10

7-(cis-3-Aminomethyl-4-chloro-1-pyrrolidinyl)-1-cyclopropyl-6-fluoro-1,4-dihydro-4-oxo-1,8-naphthyridine-3-carboxylic acid hydrochloride (compound No. 1-cis.hydrochloride)

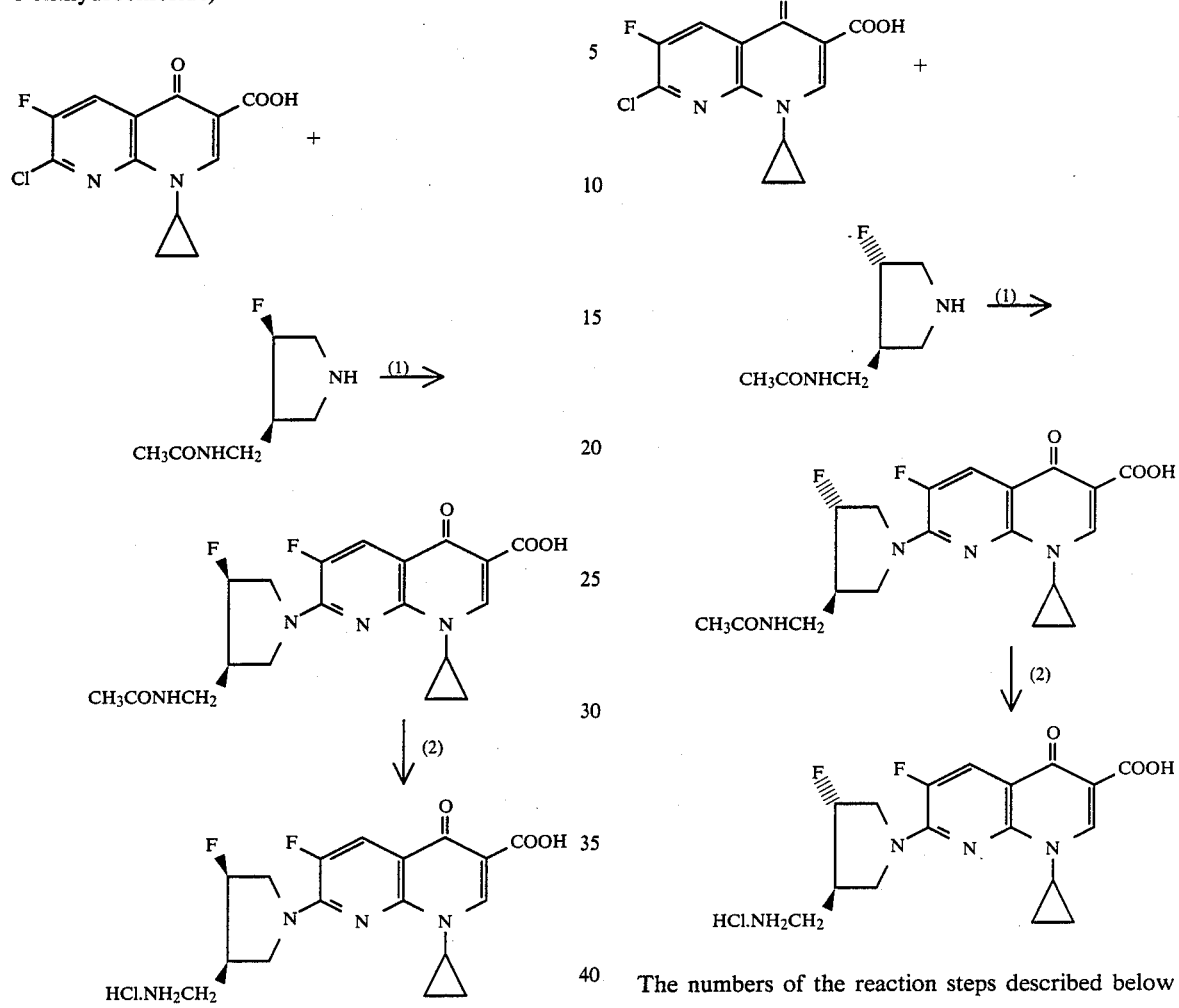

The numbers of the reaction steps described below correspond to the numbers in the above scheme.

(1) In the same manner as described in Example 3-(1), 7-(cis-3-acetylaminomethyl-4-fluoro-1-pyrrolidinyl)-1-cyclopropyl-6-fluoro-1,4-dihydro-4-oxo-1,8-naphthyridine-3-carboxylic acid was obtained from cis-3-acetylaminomethyl-1-benzyl-4-fluoropyrrolidine and 7-chloro-1-cyclopropyl-6-fluoro-1,4-dihydro-4-oxo-1,8-naphthyridine-3-carboxylic acid. m.p. 135°–137° C.

(2) In the same manner as described in Example 3-(2), 7-(cis-3-aminomethyl-4-fluoro-1-pyrrolidinyl)-1-cyclopropyl-6-fluoro-1,4-dihydro-4-oxo-1,8-naphthyridine-3-carboxylic acid hydrochloride was obtained from the above compound. m.p. 284°–286° C. (decompn.).

EXAMPLE 11

7-(trans-3-Aminomethyl-4-chloro-1-pyrrolidinyl)-1-cyclopropyl-6-fluoro-1,4-dihydro-4-oxo-1,8-naphthyridine-3-carboxylic acid hydrochloride (compound No. 1-trans.hydrochloride)

The numbers of the reaction steps described below correspond to the numbers in the above scheme.

(1) In the same manner as described in Example 3-(1), 7-(trans-3-acetylaminomethyl-4-fluoro-1-pyrrolidinyl)-1-cyclopropyl-6-fluoro-1,4-dihydro-4-oxo-1,8-naphthyridine-3-carboxylic acid was obtained from trans-3-acetylaminomethyl-1-benzyl-4-fluoropyrrolidine and 7-chloro-1-cyclopropyl-6-fluoro-1,4-dihydro-4-oxo-1,8-naphthyridine-3-carboxylic acid. m.p. 236°–238° C. (decompn.).

(2) In the same manner as described in Example 3-(2), 7-(trans-3-aminomethyl-4-fluoro-1-pyrrolidinyl)-1-cyclopropyl-6-fluoro-1,4-dihydro-4-oxo-1,8-naphthyridine-3-carboxylic acid hydrochloride was obtained from the above compound. m.p. 269°–272° C. (decompn.).

EXAMPLE 12

Ethyl 7-(cis-3-aminomethyl-4-chloro-1-pyrrolidinyl)-1-cyclopropyl-6-fluoro-1,4-dihydro-4-oxo-1,8-naphthyridine-3-carboxylate (compound No. 2-cis.ethyl ester)

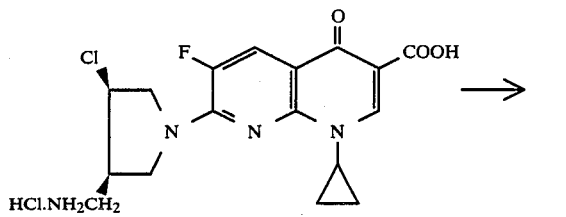

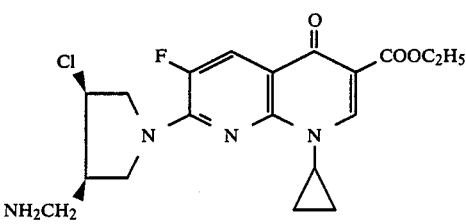

7-(cis-3-Aminomethyl-4-chloro-1-pyrrolidinyl)1-cyclopropyl-6-fluoro-1,4-dihydro-4-oxo-1,8-naphthyridine-3-carboxylic acid hydrochloride was suspended in absolute ethanol. Sulfuric acid was added to the suspension and the mixture was refluxed for 15 hours with stirring. After evaporation of ethanol, chloroform and a 20% aqueous sodium hydroxide solution were added to the residue, and the mixture was adjusted to pH 9. The organic layer was separated and chloroform was evaporated under reduced pressure. The resulting crystals were collected by filtration to give ethyl 7-(cis-3-aminomethyl-4-chloro-1-pyrrolidinyl)-1-cyclopropyl-6-fluoro-1,4-dihydro-4-oxo-1,8-naphthyridine-3-carboxylate, m.p. 163°–167° C.

EXAMPLE 13

Isopropyl 7-(cis-3-aminomethyl-4-chloro-1-pyrrolidinyl)-1-cyclopropyl-6-fluoro-1,4-dihydro-4-oxo-1,8-naphthyridine-3-carboxylate (compound No. 2-cis-isopropyl ester)

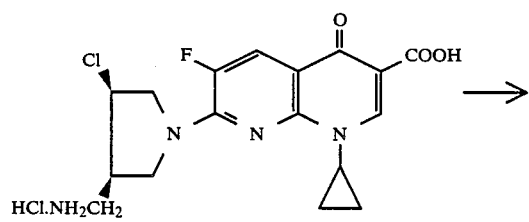

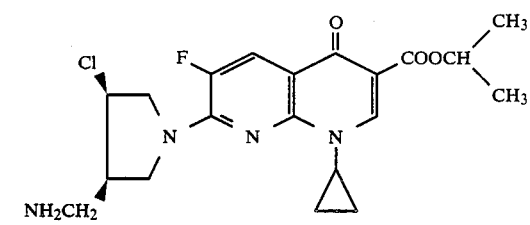

In the same manner as described in Example 12 except that isopropyl alcohol was used in place of ethanol, isopropyl 7-(cis-3-aminomethyl-4-chloro-1-pyrrolidinyl)1-cycylopropyl-6-fluoro-1,4-dihydro-4-oxo-1,8-naphthyridine-3-carboxylate was obtained. m.p. 172°–74° C.

Examples 14 to 16 show pharmaceutical preparations containing the compounds of this invention and active ingredients. Compound No. 1-cis.hydrochloride or compound No. 2-cis.hydrochloride are as defined hereinafter.

EXAMPLE 14

| | |
|---|---|
| Compound No. 1-cis.HCl or compound No. 2-cis.HCl | 250 g |
| Starch | 50 g |
| Lactose | 35 g |
| Talc | 15 g |

The above components were blended with ethanol and granulated and filled into 1,000 capsules in accordance with conventional methods.

EXAMPLE 15

| | |
|---|---|
| Compound No. 1-cis.HCl or compound No. 2-cis.HCl | 250 g |
| Starch | 54 g |
| Calcium carboxymethyl cellulose | 40 g |
| Microcrystalline cellulose | 50 g |
| Magnesium stearate | 6 g |

The above components were blended with ethanol, granulated and made into tablets in a manner known per se.

Thus, 1,000 tablets each weighing 400 mg were formed.

Example 16

| | |
|---|---|
| Compound No. 1-cis.HCl | 50 g |
| Lactic acid | 120 g |

The above components were dissolved in distilled water sufficient to make a ten-liter solution. The solution was adjusted to pH about 4 with an aqueous sodium hydroxide solution, and then filled in ampoules (10 ml) to make an injectable solution.

The chemotherapeutic activities of the compounds of this invention are shown in Examples 17 and 18 hereinbelow in comparison with known antibacterial agents. The compounds tested comprise:

Compound No. 1-cis.hydrochloride: 7-(cis-3-aminomethyl-4-fluoro-1-pyrrolidinyl)-1-cyclopropyl-6-fluoro-1,4-dihydro-4-oxo-1,8-naphthyridine-3-carboxylic acid hydrochloride, Compound No. 1-trans.hydrochloride: 7-(trans-3-aminomethyl-4-fluoro-1-pyrrolidinyl)-1-cyclopropyl-6-fluoro-1,4-dihydro-4-oxo-1,8-naphthyridine-3carboxylic acid hydrochloride, Compound No. 2-cis.hydrochloride: 7-(cis-3-aminomethyl-4-chloro-1-pyrrolidinyl)-1-cyclopropyl6-fluoro-1,4-dihydro-4-oxo-1,8-naphthyridine-3-carboxylic acid hydrochloride, Compound No. 4-trans.hydrochloride: 1-cyclopropyl-7-(trans-3-ethylaminomethyl-4-fluoro-1-pyrrolidinyl)-6-fluoro-1,4-dihydro-4-oxo-1,8-naphthyridine-3-carboxylic acid hydrochloride, Compound A: 7-(3-aminomethyl-1-pyrrolidinyl)-1-ethyl-6-fluoro-1,4-dihydro-4-oxo-1,8-naphthyridine-3-carboxylic acid hydrochloride, the free form of which is disclosed in Example 1 of E. P. Laid Open No. 106489,

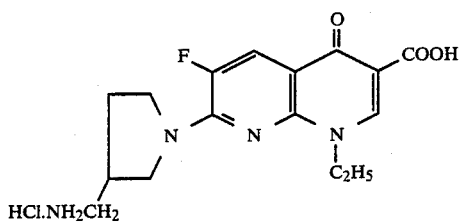

Compound B: 7-(3-aminomethyl-1-pyrrolidinyl)-1-cyclopropyl-6-fluoro-1,4-dihydro-4-oxo-1,8-naphthyridine-3-carboxylic acid hydrochloride, the free form of which is disclosed in Example 55 of E. P. Laid Open No. 153163.

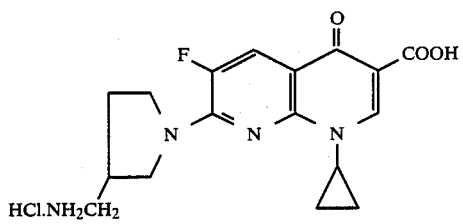

EXAMPLE 17

The antibacterial activity in vitro is show in Table 1. The numbers in the table show minimum inhibitory concentrations (MIC) (μg/ml), calculated for free base. The minimum inhibitory concentration was determined by the twofold agar-dilution method, which was recommended by Japan Society of Chemotherapy (Chemotherapy, 29(1), 76(1981)), using Muller-Hinton agar. One loopful of an overnight culture of test organisms in Mueller-Hinton broth was inoculated onto 10-ml drug-containing agar layers in petri dishes. Bacterial inocula contained approximately $10^6$ colonyl-forming units. Bacterial growth was observed after 20-hour incubation at 37° C. The MIC was defined as the lowest drug concentration which prevented visible bacterial growth.

TABLE 1

| | | In vitro antibacterial activity | | | | | |
|---|---|---|---|---|---|---|---|
| | | Compounds | | | | | |
| | Strains | No. 1-cis.HCl | No. 1-trans.HCl | No. 2-cis.HCl | No. 4-trans.HCl | A | B |
| Gram + | S. aureus Smith | 0.025 | 0.025 | 0.025 | 0.025 | 0.1 | 0.05 |
| | S. aureus 50774 | 0.025 | 0.025 | 0.025 | 0.025 | 0.2 | 0.025 |
| | S. aureus 80 | 0.025 | 0.025 | 0.0125 | 0.0125 | 0.39 | 0.05 |
| | S. epidermidis 8 | 0.0125 | 0.0125 | 0.0125 | 0.0125 | 0.1 | 0.025 |
| | S. pyogenes A65 | 0.0125 | 0.025 | 0.025 | 0.05 | 0.39 | 0.05 |
| Gram − | E. coli P-5101 | 0.0125 | 0.0063 | 0.0125 | 0.0125 | 0.39 | 0.025 |
| | E. coli P-51208 | 0.78 | 0.78 | 0.78 | 0.78 | 6.25 | 3.13 |
| | E. coli P-51209 | 0.78 | 0.78 | 0.78 | 0.78 | 12.5 | 3.13 |
| | P. rettgeri IFO 3850 | 0.05 | 0.05 | 0.05 | 0.05 | 0.78 | 0.1 |
| | K. pneumoniae 13 | 0.05 | 0.05 | 0.05 | 0.05 | 0.39 | 0.1 |
| | M. lacunata P-7102 | 6.25 | 3.13 | 3.13 | 3.13 | 50 | 12.5 |

EXAMPLE 18

In vivo efficacy against systemic infections in mice is shown in Table 2.

Compounds were each dissolved in deionized water. Each of the solutions was intravenously (iv) administered to mice infected by each of the test organisms under the conditions shown hereinbelow, and the median effective dose ($ED_{50}$) was calculated by probit analysis. The numerals in the table show $ED_{50}$ (mg/kg) value, caluclated for free base.

Experimental conditions:
Mice: Male mice (ddY-S) weighing about 20 g
Infection:
  Staphylococcus aureus 50774
    Intravenous infection with $5 \times 10^8$ cells per mouse suspended in saline.
  Streptococcus pyogenes A65
    Intraperitoneal infection with $3 \times 10^7$ cells per mouse suspended in brain heart infusion broth.
Medication:
  Twice, immediately and 6 hours after infection.
Observation:
  For 14 days in the case of Staphylococcus aureus 50774. For 7 days in the case of Streptococcus pyogenes A65.

TABLE 2

| | In vivo efficacy against systemic infections in mice | | | | |
|---|---|---|---|---|---|
| | Compounds | | | | |
| Strains | No. 1-cis.HCl | No. 2-cis.HCl | No. 4-trans.HCl | A | B |
| S. aureus 50774 | 0.274 | 0.355 | — | 2.79 | 0.701 |
| S. pyogenes A65 | 0.365 | 0.235 | 0.267 | 3.75 | 0.601 |

EXAMPLE 19

Solubility in water is shown in Table 3.

The sample was added to distilled water (10 ml) and the solution was shaken in the supersaturated state for 30 minutes. After incubation at 25° C. overnight, the solution was filtered with a microfilter. The filtrate was diluted with 0.1 N hydrochloric acid. The absorbance at 270 nm of the solution was measured and the concentration (μg/ml) of the sample was calculated from a calibration curve separately prepared.

TABLE 3

| Compounds | Solubility in water Solubility (μg/ml) |
|---|---|
| No. 1-cis | 927 |
| No. 2-cis | 713 |
| No. 3-cis | 789 |

What is claimed is:

1. A 1,8-naphthyridine derivative of the formula

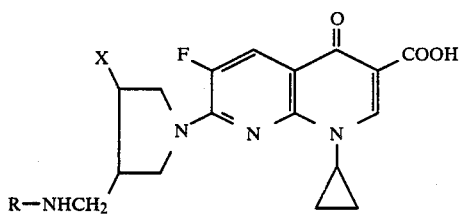

wherein X is a fluorine or chlorine atom, and R is a hydrogen atom, or a methyl or ethyl group; or a pharmaceutically acceptable ester or a pharmaceutically acceptable salt thereof.

2. A 1,8-naphthyridine derivative of the formula

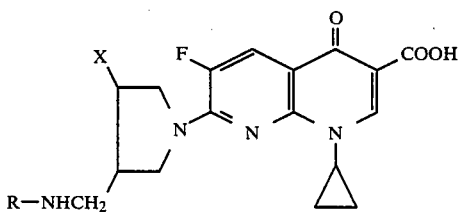

wherein X is a fluorine or chlorine atom, and R is a hydrogen atoms, or a methyl or ethyl group; or a pharmaceutically acceptable salt thereof.

3. A $C_1$–$C_5$ alkyl ester of a 1,8-naphthyridine derivative of the formula

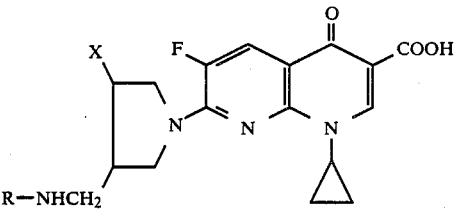

wherein X and R are as defined above; or a pharmaceutically acceptable salt thereof.

4. 7-(3-Aminomethyl-4-fluoro-1-pyrrolidinyl)-1-cyclopropyl-6-fluoro-1,4-dihydro-4-oxo-1,8-naphthyridine-3-carboxylic acid or a pharmaceutically acceptable acid addition salt thereof.

5. 7-(3-Aminomethyl-4-chloro-1-pyrrolidinyl)-1-cyclopropyl-6-fluoro-1,4-dihydro-4-oxo-1,8-naphthyridine-3-carboxylic acid or a pharmaceutically acceptable acid addition salt thereof.

6. 1-Cyclopropyl-7-(3-ethylaminomethyl-4-fluoro-1-pyrrolidinyl)-6-fluoro-1,4-dihydro-4-oxo-1,8-naphthyridine-3-carboxylic acid or a pharmaceutically acceptable acid addition salt thereof.

7. An antibacterial composition comprising as an active ingredient an antibacterially effective amount of a compound or ester or salt thereof as defined in claim 1 and a pharmaceutically acceptable carrier therefor.

8. A method for the treatment of a bacterial infectious disease which comprises administering an antibacterially effective amount of a compound or ester of salt thereof as defined in claim 1 to a warm-blooded animal.

* * * * *